United States Patent [19]

Ender

[11] Patent Number: 5,135,527
[45] Date of Patent: Aug. 4, 1992

[54] INSTRUMENTARIUM FOR REPOSITIONING AND FIXING PETROCHANTEROUS AND SUBTROCHANTEROUS FRACTURES

[76] Inventor: Hans G. Ender, Krenngasse 3, Vienna, Austria, A-1180

[21] Appl. No.: 602,657

[22] Filed: Oct. 24, 1990

[30] Foreign Application Priority Data

Oct. 25, 1989 [AT] Austria .................. 2462/89

[51] Int. Cl.⁵ .................................. A61B 17/58
[52] U.S. Cl. ............................. 606/62; 606/67
[58] Field of Search ............... 606/67, 60, 62, 66, 606/72

[56] References Cited

U.S. PATENT DOCUMENTS

| | | | |
|---|---|---|---|
| 4,712,541 | 12/1987 | Harder et al. | 606/67 |
| 4,805,607 | 2/1989 | Engelhardt et al. | 606/67 |
| 4,915,092 | 4/1990 | Firica et al. | 606/67 |

FOREIGN PATENT DOCUMENTS

| | | | |
|---|---|---|---|
| 95990 | 12/1983 | European Pat. Off. | 606/62 |
| 824377 | 12/1951 | Fed. Rep. of Germany | 606/62 |
| 2459257 | 12/1975 | Fed. Rep. of Germany | 606/67 |
| 3144210 | 5/1983 | Fed. Rep. of Germany | 606/62 |
| 576249 | 6/1976 | Sweden | 606/62 |
| 1647 | 6/1981 | World Int. Prop. O. | 606/62 |

*Primary Examiner*—Robert A. Hafer
*Assistant Examiner*—Kevin G. Rooney
*Attorney, Agent, or Firm*—Fleit, Jacobson, Cohn, Price, Holman & Stern

[57] ABSTRACT

An insert member of use in an impact hole leading into a medullary canal of a bone for treating a fracture by insertion of at least one bone nail into the medullary canal is disclosed. The insert member has a guide channel for receiving the proximal end of the bone nail, lateral openings and a pin for fixing the insert member in the impact hole, and a closure member for the proximal end of the guide channel. The closure member includes an abutment for the proximal end of the bone nail which allows limited reverse movement of the proximal end of the bone nail within the guide channel. The abutment may be a separate member attached to the closure member by a spring or the abutment may be a shaped projection extending forwardly from the closure member.

6 Claims, 2 Drawing Sheets

INSTRUMENTARIUM FOR REPOSITIONING AND FIXING PETROCHANTEROUS AND SUBTROCHANTEROUS FRACTURES

BACKGROUND OF THE INVENTION

1. Field of the Invention

The invention relates to an instrumentarium for repositioning and fixing of pertrochanterous and subtrochanterous fractures, comprising at least one bone nail of resilient material, which nail is bent at least at its proximal end portion and which is insertable into the medullary canal of a bone through an impact hole formed in the bone and which abuts under tension with its apex of curvature the wall of the medullary canal opposing the impact hole, the distal end of the bone nail being provided with a coupling member allowing a non-rotatable connection with an impact tool, an insert member insertable into the impact hole having a guiding channel for the bone nail to be driven in and for the at least partial accommodation of the coupling member of the bone nail, the insert member further being provided with a fixing means preventing its shifting in the impact hole and with a closure member for closing the guiding channel.

2. Description of the Prior Art

It is known to reposition and to fix pertrochanterous and subtrochanterous fractures by opening the medullary canal of the bone through an impact hole and by introducing into this impact hole at least one bone nail, conveniently several bone nails consisting of elastic material and being bent at least in its (their) proximal area. When introducing such bone nails into the medullary canal, the nails, under tension due to their elasticity, contact the wall of the medullary canal opposing the impact hole, so that on the proximal point of each nail arriving at the site of the fracture, the nail passes beyond this fracture into the condyle of the bone and fixes the fracture. By rotating the individual nails, the bone portions can be reduced so that they assume the correct relative position at the site of the fracture. For this purpose, the distal end of each nail is provided with a coupling member allowing a wholly non-rotatable connection with an impact tool. It is known to give this coupling member the shape of a small plate-like flattening U.S. Pat. No. 4,055,172), although other embodiments of the coupling member are possible. When the known nails are correctly positioned in the medullary canal, the nail ends protrude from the impact hole and the coupling member abuts under tension the outer surface of the bone distally of the impact hole, so that there exists the danger, particularly for older persons having porous bones, that the bone may collapse at the abutment site and moreover the sinews and muscles extending above the impact hole will be irritated by the protruding distal nail ends.

As a rule, the impact hole is made such that the bone is first punctured and subsequently the small hole thus formed is widended by means of a three- or four-edged reamer, enlarged by means of a chisel or by means of a drill. In all these cases, parts of the bone can be split off, thus enlarging the impact hole in an undesired manner. But also when forcibly driving the nails, a cortical wedge can be split off the proximal cortex by tangential shearing stress, which results in an undesired enlargement of the impact hole so that the edge of the impact hole can also collapse on its front side. Both cases result in the nails protruding in an uncontrolled manner and if the fracture extends into the bone, a torsional fracture of the femur may be produced by the surgeon.

It can also occur that the bone nails are driven too far into the impact hole so that the coupling member no longer abuts the outer surface of the bone or that the coupling member abutting the outer surface of the bone shifts towards the medullary canal because part of the edge of the hole has been broken off.

If the coupling member enters the interior of the medullary canal and thus disappears within the bone, this invariably results in the drawback that the required tension stress of the nails is reduced and the desired effect is thus no longer assured. If the whole nail is located within the medullary canal, it may be caught by the spongiosa bubbles present in the medullary canal and thereby prevented from sliding distally. If in such a case the bone is loaded so that the bone portions are brought closer together at the fracture site, the nail tip may perforate the condyle of the bone and penetrate into the socket of the hip joint (acetabulum). If nails having wholly entered the medullary canal are not caught by the spongiosa bubbles, the nails slide in distal direction and can then be removed only with great difficulty. For removing such nails, the impact hole must be enlarged to such an extent that the distal end of the nail located within the medullary canal can be seized.

In order to prevent these difficulties, it has been proposed to provide an insert member insertable into the impact hole and provided with a guiding channel for the bone nail to be driven in and for the at least partial accommodation of the coupling member of the bone nail and fixed to the bone by a fixing means, for instance a screw. After insertion of the bond nail(s), the insert member is closed by means of a lid-shaped closure member preventing the shifting of the distal nail ends out of the insert member (U.S. Pat. No. 4,467,793). The disadvantage of this known embodiment resides in the fact that the bone nails shift in the medullary canal until their distal ends abut the side of the closure member facing the guiding channel where the position of the bone nails is fixed. On loading the bone, however, the bone fragments are brought close together at the fracture site and it is then convenient to shift the bone nails in a distal direction in order to prevent the nail tip from perforating the condyle, although the shifting must not be so great as to disturb the function of the bone nails.

BRIEF SUMMARY OF THE INVENTION

It is thus the object of the invention to improve an instrumentarium of the type initially mentioned by assuring a defined and limited shift of the bone nails inserted into the medullary canal in particular on subjecting the leg to stress, so that when the distal end of a bone nail is located at a larger distance from the side of the closure member facing the guiding channel, a comparatively unhindered movement of this nail in its longitudinal direction is possible, while when the distal end of the nail approaches the side of the closure member facing the guiding channel, this movement encounters increased resistance until it is finally completely inhibited.

BRIEF DESCRIPTION OF THE DRAWINGS

The invention will now be described in detail with reference to the accompanying drawings showing embodiments of the invention.

DESCRIPTION OF THE PREFERRED EMBODIMENTS

Figure 1:
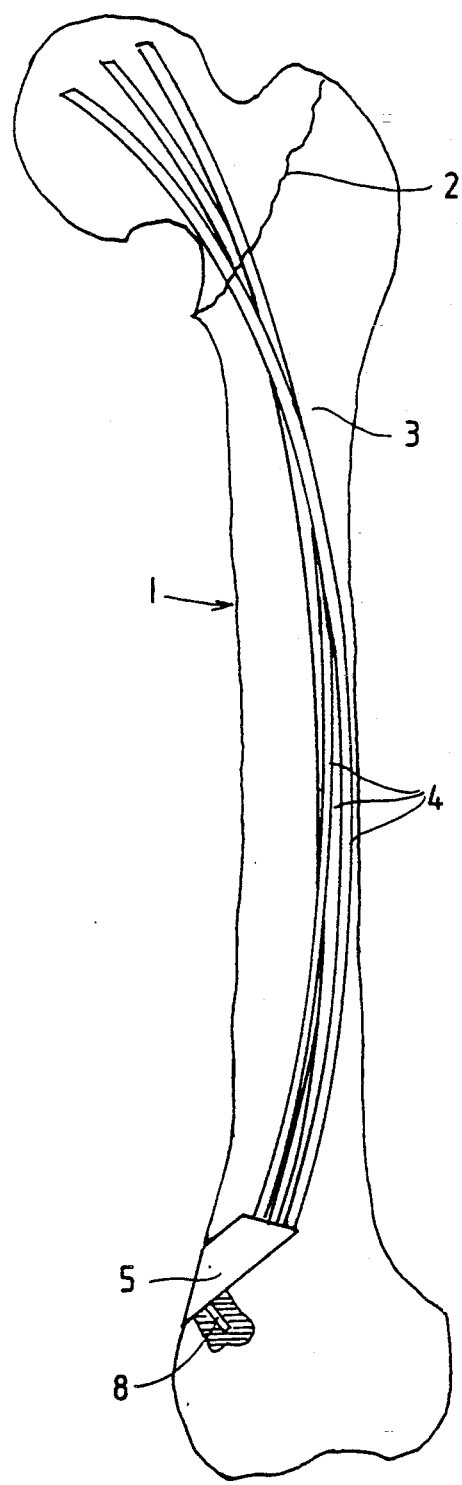
FIG. 1 shows an instrumentarium according to the invention arranged in a bone having a fracture.
Figure 2:
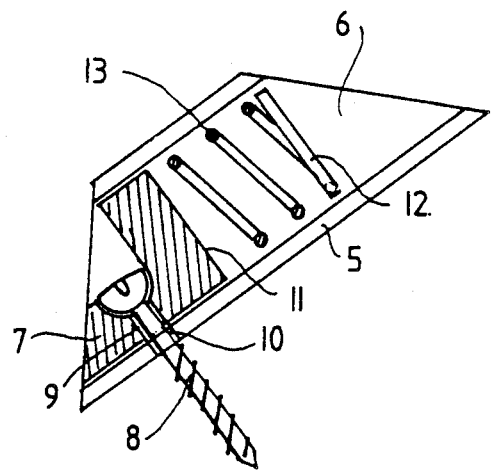
FIGS. 2 to 5 represent longitudinal sections of various embodiments of the insert member according to the invention provided with a closure member.

FIG. 1 shows a bone 1 having a fracture 2. For repositioning and fixing the fracture 2, three bone nails 4 consisting of elastic material and bent in their proximal end portion are inserted into the medullary canal 3 of the bone 1. To this end, the medullary canal is opened by puncturing at the knee joint area of the bone and an impact hole is then milled or bored by means of a milling cutter or a drill, the axis of the hole being so selected that the nails 4 can be driven in the required direction. Subsequently, an insert member 5 is inserted into the impact hole, ten the bone nails are driven in and rotated for reducing the fracture site. For this purpose, the bone nails are provided at their respective distal ends with a coupling member (not shown) permitting a wholly non-rotatable connection with an impact tool. The insert member 5 is provided with a guiding channel (see FIGS. 2 to 5) which is arranged so that the nails driven in arrive in the medullary canal 3 in the desired manner. The nails 4 are driven in so far that their distal end provided with the coupling member is received by the guiding channel, thus does not protrude to the outside and does not irritate the sinews and muscles positioned above the impact hole.

The insert member 5 is closed by means of a closure member 7. The insert member 5 and the closure member 7 are fixed by means of a screw 8 screwed into the bone and extending essentially perpendicularly to the axis of the guiding channel 6 and penetrating an opening 9 in the closure member 7 as well as an opening 10 aligned therewith in the insert member. A screw 8 like this is usually required for fixing the insert member, so that a single screw serves for attaching the insert member 5 as well as the closure member 7 to the bone.

The side 11 of the closure member 7 facing the guiding channel is provided with means limiting a shifting of the bone nails 4 present in the medullary canal 3 as a function of the position of the distal ends of the nails in the insert member.

In the embodiment according to FIG. 1, a supporting body 12 connected to the closure member 7 by a helical spring 13 is provided for supporting the distal nail ends. When the nails 4 shift in the direction of the closure member 7, the helical spring is compressed via the distal nail ends and the shifting is opposed by increased resistance.

Figure 3:
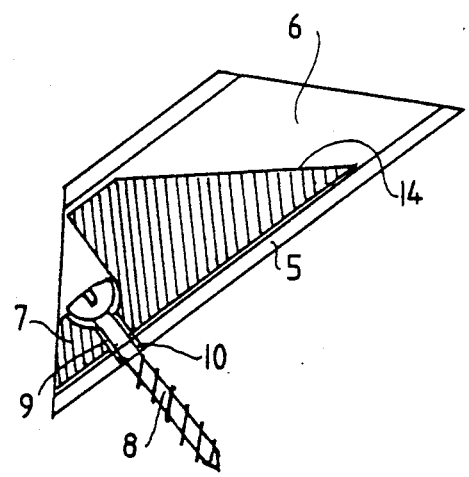

In the embodiment according to FIG. 3, the closure member 7 is provided on its side 11 facing the guiding channel with an inclined surface 14 facing upwards on which the distal nail ends are supported. If these distal nail ends slide along the inclined surface 14 due to a shifting of the nails, the curvature of the bone nails 4 consisting of elastic material and thus also the tension with which the bone nails abut the wall of the medullary canal 3 changes, so that the friction on the wall of the medullary canal is increased and the shifting is thus opposed by increased resistance.

Figure 4:
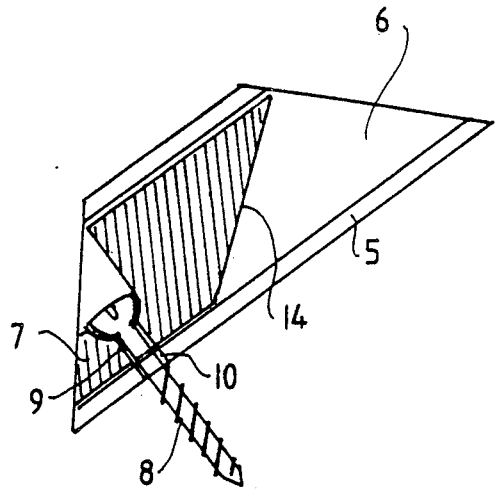

The embodiment according to FIG. 4 differs from the embodiment according to FIG. 3 in that the inclined surface faces downwards.

Figure 5:
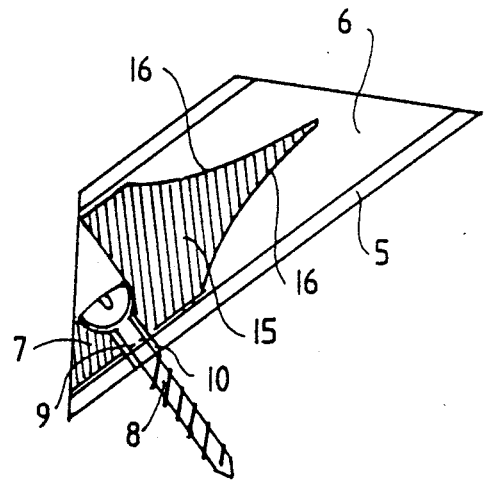

The embodiment according to FIG. 5, the side of the closure member 7 facing the guiding channel 6 is provided with a projection 15 formed rotationally symmetrical in relation to the axis of the guiding channel and provided with inclined surfaces 16 on all sides along which the distal nail ends slide during their shifting in the direction to the closure member 7, the curvature of the bone nails consisting of elastic material and thus the resistance to a shifting changing independent of the position which said distal nail ends occupy in the guiding channel 6.

What is claimed is:

1. An insert member for use in an impact hole leading into a medullary canal of a bone for treating a fracture by insertion of at least one bone nail into the medullary canal, the insert member including a guide channel for receiving a distal end portion of a bone nail, fixing means for preventing shifting of the insert member in the impact hole, a closure member for closing one end of the guide channel, and abutment means for the distal end of the bone nail associated with the closure member for accommodating limited movement of the bone nail within the guide channel wherein the abutment means comprises an abutment body connected to the closure member by elastic means.

2. An insert member according to claim 1 wherein the elastic means comprises a spring.

3. An insert member for use in an impact hole leading into a medullary canal of a bone for treating a fracture by insertion of at least one bone nail into the medullary canal, the insert member including a guide channel for receiving a distal end portion of a bone nail, fixing means for preventing shifting of the insert member in the impact hole, a closure member for closing one end of the guide channel, and abutment means for the distal end of the bone nail associated with the closure member for accommodating limited movement of the bone nail within the guide channel wherein the abutment means comprises an inclined surface formed on the closure member.

4. An insert member for use in an impact hole leading into a medullary canal of a bone for treating a fracture by insertion of at least one bone nail into the medullary canal, the insert member including a guide channel for receiving a distal end portion of a bone nail, fixing means for preventing shifting of the insert member in the impact hole, a closure member for closing one end of the guide channel, and abutment means for the distal end of the bone nail associated with the closure member for accommodating limited movement of the bone nail within the guide channel wherein the abutment means comprises a projection extending from the closure member and decreasing in cross-sectional area towards an opposite end of the guide channel.

5. An insert member according to claim 4 wherein the projection is symmetrical in relation to a longitudinal axis of the guide channel.

6. An insert member for use in an impact hole leading into a medullary canal of a bone for treating a fracture by insertion of at least one bone nail into the medullary canal, the insert member including a guide channel for receiving a distal end portion of a bone nail, fixing means for preventing shifting of the insert member in the impact hole, a closure member for closing one end of the guide channel, and abutment means for the distal end of the bone nail associated with the closure member for accommodating limited movement of the bone nail within the guide channel, wherein the fixing means comprises a lateral aperture through a wall of the guide channel and a pin-like fastener element for insertion through said aperture into the bone and a further lateral aperture in he closure member and wherein the fastener element is adapted to fit through both said apertures into the bone.

* * * * *